(12) United States Patent
Anitua Aldecoa (10) Patent No.: US 11,766,645 B2
(45) Date of Patent: Sep. 26, 2023

(54) FLUID MIXING DEVICE AND MIXING METHOD

(71) Applicant: BIOTECHNOLOGY INSTITUTE, I MAS D, S.L., Vitoria (ES)

(72) Inventor: Eduardo Anitua Aldecoa, Vitoria (ES)

(73) Assignee: BIOTECHNOLOGY INSTITUTE, I MAS D, S.L., Vitoria (ES)

( * ) Notice: Subject to any disclaimer, the term of this patent is extended or adjusted under 35 U.S.C. 154(b) by 643 days.

(21) Appl. No.: 16/730,437

(22) Filed: Dec. 30, 2019

(65) Prior Publication Data
US 2020/0206703 A1 Jul. 2, 2020

(30) Foreign Application Priority Data
Dec. 28, 2018 (ES) ................. ES201831290

(51) Int. Cl.
| | | |
|---|---|---|
| B01F 25/451 | (2022.01) | |
| B01F 31/441 | (2022.01) | |
| A61J 1/20 | (2006.01) | |
| B01F 23/41 | (2022.01) | |
| B01F 33/501 | (2022.01) | |
| B01F 35/42 | (2022.01) | |

(Continued)

(52) U.S. Cl.
CPC ........... *B01F 31/441* (2022.01); *A61J 1/2096* (2013.01); *B01F 23/41* (2022.01); *B01F 25/4512* (2022.01); *B01F 33/50112* (2022.01); *B01F 35/2202* (2022.01); *B01F 35/42* (2022.01); *A61J 2200/70* (2013.01); *B01F 2101/2202* (2022.01)

(58) Field of Classification Search
CPC .............. B01F 25/4512; A61J 1/2096
USPC .................... 366/176.3, 176.4, 268
See application file for complete search history.

(56) References Cited

U.S. PATENT DOCUMENTS

| | | | | |
|---|---|---|---|---|
| 3,035,820 A | * | 5/1962 | Todd .................. | B01F 25/4512 366/334 |
| 3,071,351 A | * | 1/1963 | Brown .................. | B01F 23/41 366/268 |

(Continued)

FOREIGN PATENT DOCUMENTS

| | | |
|---|---|---|
| CN | 106729679 | 5/2017 |
| ES | 2633815 | 9/2017 |

(Continued)

OTHER PUBLICATIONS

Spanish Search report dated Mar. 11, 2019, in corresponding application No. 201831290.

*Primary Examiner* — David L Sorkin
(74) *Attorney, Agent, or Firm* — Browdy and Neimark, PLLC (57) ABSTRACT

Mixing device (1) and fluid mixing method, by means of successive transfers between syringes. The mixing method comprises placing a pair of syringes (2, 3) in the mixing device (1), adjusting a variable fixing element adaptable to the pair of syringes (2, 3) and selecting and running a mixing programme, being the mixing force, the speed and the range and the number of transfers adjustable. The mixing device comprises a mobile carriage (7) longitudinally movable and fixing elements (8, 9) with an adjustable distance between them. The invention allows for the mixing or emulsifying of blood fluids with different viscosity, particularly a protein gel and a platelet-rich plasma, for the preparation of dermatological formulations, in a versatile, hygienic and effective manner.

10 Claims, 8 Drawing Sheets

(51) Int. Cl.
*B01F 35/22* (2022.01)
*B01F 101/00* (2022.01)

(56) References Cited

U.S. PATENT DOCUMENTS

| | | | |
|---|---|---|---|
| 7,748,892 B2* | 7/2010 | McCoy | B02C 19/08 |
| | | | 141/270 |
| 9,073,021 B2* | 7/2015 | Nakamura | B01F 31/65 |
| 2002/0101785 A1* | 8/2002 | Edwards | B01F 25/4512 |
| | | | 604/82 |
| 2005/0213427 A1 | 9/2005 | Steckle, Jr. et al. | |
| 2017/0326293 A1 | 11/2017 | Sims et al. | |

FOREIGN PATENT DOCUMENTS

| | | |
|---|---|---|
| JP | S4970562 U | 6/1974 |
| JP | 2016158542 | 9/2016 |
| KR | 20180132255 | 12/2018 |
| WO | 02058834 | 8/2002 |
| WO | 2016077538 | 5/2016 |

* cited by examiner

FLUID MIXING DEVICE AND MIXING METHOD

FIELD OF THE INVENTION

This invention falls within the field of laboratory devices and, in particular, biofluid mixing devices. The invention relates to a mixing device that allows for a quick and reproducible mixing or emulsifying of biofluids, for example autologous fluids obtained from a the plasma of a patient. The invention also relates to a method of mixing biofluids for obtaining a formulation for topical or injectable applications.

PRIOR ART

At present, there are techniques and equipment, used in laboratories or aesthetic clinics for obtaining autologous fluids extracted from the blood of a patient, such as platelet-rich plasma gel. For this purpose, centrifugation equipment can be used, which allow for the separation of the different components of the patient's blood for later use. One example of the use of compositions made from a patient's plasma is dermatological or beauty treatment. There are protocols for obtaining plasma gel and for its subsequent use by intradermal injections for the elimination of facial wrinkles. These protocols are usually based on the fractioning of the patient's blood by centrifuging, followed by subsequent handle by a clinical specialist before the final product is injected into the patient.

Once the fluids have been extracted from the blood, they have to be correctly mixed or emulsified to obtain the commercial product or final formulation to be delivered to the patient. Syringes of various sizes, containing the product to be emulsified or supplied, can be used both for the previous emulsification and for delivery to the patient.

There are also various infusion pumps on the market to control the supply of the syringe contents. The WO2016077538A1 publication discloses an example of an infusion pump, adapted for use with syringes, being this invention based on a motor system that controls the movement of a carriage carrying a syringe, with respect to a casing, for the supply of the fluid of the syringe to a patient. Equipment such as the one described in the aforementioned publication does not provide a solution to a correct emulsification of the product, prior to its application to the patient.

Moreover, the protocols known for this type of application have a certain lack of reproducibility of the products obtained and an undesirable excess of handling, which can cause unwanted contamination of the product finally supplied to the patient. In order to try to overcome these limitations, there are mixing devices that allow fluids to be emulsified automatically or semi-automatically, facilitating the preparation of formulations ready to be supplied and preventing the need to have to emulsify or mix the fluids manually. These devices allow content transfers between two faced syringes and allow configurable parameters, such as the adjustment of the mixing speed. However, they are usually specifically designed for a certain size of syringe, generally resulting in limited versatility.

The objective of the present invention is to provide a device that allows an efficient mixture or emulsion of plasma components, providing some improvement concerning the versatility of the mixing procedure.

BRIEF DESCRIPTION OF THE INVENTION

The object of the invention is a method and a mixing device for mixing or emulsifying fluids, by means of successive transfers between syringes with a certain transfer range. The mixing device according to the invention comprises at least one mobile carriage, movable in a longitudinal direction and provided with a casing configured to accommodate and retain at least one pair of syringes. These syringes are connected faced to each other, connected to each other by a first end of each syringe and alignedly arranged. The mixing device additionally comprises at least two fixing elements, located one on each side of the mobile carriage and adapted to accommodate and retain a second free end of each syringe. At least one of the fixing elements is adjustable, being adapted to accommodate and retain the free end of the corresponding syringe in a movable position along the longitudinal direction. In this way, the distance between the two fixing elements can be adjusted variably. For carrying out a transfer programme, the mixing device comprises a control unit, communicated with a set of sensors and a mechanism for the transmission of a linear displacement to the mobile carriage triggered by a control signal generated by the control unit. This set of sensors comprises a calibration sensor, for the automatic calibration of the range of each transfer and at least one inversion sensor, which allows for the inversion of the direction of displacement of the mobile carriage.

Like some known mixers, the device of the invention allows for mixing, emulsifying and/or homogenizing fluids, preferably components present in the blood of a patient, by transferring the fluids between a pair of connected syringes. However, compared with existing devices, the mixing device according to the invention provides remarkable versatility from multiple points of view.

On one hand, the device allows various parameters to be adjusted: the force of the internal motor, depending on the viscosity of the fluids to be mixed, the number of transfers and an adjustable speed of for transfers according to pre-set programmes. The fact of allowing for an automatic and versatilely configurable mixture or emulsion, makes it possible to obtain a final product with the appropriate biomechanical characteristics of viscosity, applicability and texture, regardless of the clinical specialist who makes the mixture or emulsion. Thereby, the mixing device according to the invention significantly facilitates the manufacture procedure of the final product, reduces preparation times and eliminates the variability derived from the involved clinical specialist.

The mixing device of the invention allows the mixing or emulsion of fluids extracted from a patient's blood, particularly protein gel and platelet-rich plasma, for the production of products or formulations. These fluids, once mixed using the device of the invention, are applicable by topical application or injected subdermally or intradermally for the treatment, for example, of different types of facial wrinkles. Although the mixing device of the invention has been specifically designed to mix blood compounds extracted from the patient's blood, the mixing device can be used for the emulsion or mixing of other types of fluids that require similar characteristics.

The mixing device of the invention is compatible with standard syringes of different sizes, for example syringes with volumes between 1 ml to 60 ml from different manufacturers. Additionally, thanks to the adjustable configuration of the fixing elements, the mixing device of the invention has a very advantageous feature in the sense of allowing for a variable loading or variable filling levels of the syringes. This variability regarding the volume of mixing is particularly advantageous when mixing variable blood components, depending on the patient's blood type.

The mixing method according to the invention comprises the following steps: loading at least one pair of syringes faced to each other with the fluids to be mixed; placing the pair of syringes in the mixing device; adjusting the position of the adjustable fixing element and fixing the pair of syringes to the fixing elements; selecting a mixing programme, which comprises a predefined number of transfers with a variable and predetermined speed for each transfer and running the selected mixing programme.

The invention allows for the mixing of autologous fluids with different viscosities. According to the preferred embodiments of the invention, the mixed fluids are a protein gel and an activated plasma, both obtained from the patient's blood. In summary, the mixing device and the mixing method according to the invention provide an optimal emulsion of two different plasma components obtained from the patient's own blood, thanks to the fact that the mixing device has a flexible configuration that makes it possible to adjust a high mechanical force required for the correct homogenization of fluids of different viscosity, such as the aforementioned protein gel (solid phase) and activated plasma (liquid phase). This makes the mixing device of the invention a key piece of equipment for the preparation of topical or injectable formulations.

The correct mixing of both components leads to get a product or formulation obtained 100% autologously and prepared in situ. The invention has additional advantages in terms of hygiene and sterility, since the mixed product can be used directly for treatment, for example dermal treatment, by injecting the product directly into the patient by means of one of the syringes used in the mixing device. In this way, additional transfers of the final products are avoided, minimizing possible contamination and keeping the product in a sterile state.

In this invention, the mixed fluids may comprise liquid phases, substances or cells in suspension. The result of a mixing operation of two fluids is an emulsion wherein one fluid is dispersed in another fluid. Therefore, the term mixing should be understood in a broad sense, also comprising the concept of emulsifying and/or homogenizing.

BRIEF DESCRIPTION OF THE FIGURES

The details of the invention can be seen in the accompanying figures, non-limiting the scope of the invention.

DETAILED DESCRIPTION OF THE INVENTION

The object of the invention is a mixing device and a method for mixing, emulsifying and/or homogenizing two or more fluids efficiently and reproducibly. The fluids to be mixed are transferred between pairs of syringes, being these syringes connected faced to each other and placed in the mixing device (1) according to the invention. The definition of transfer will be detailed below, for greater clarity.

Figure 1:
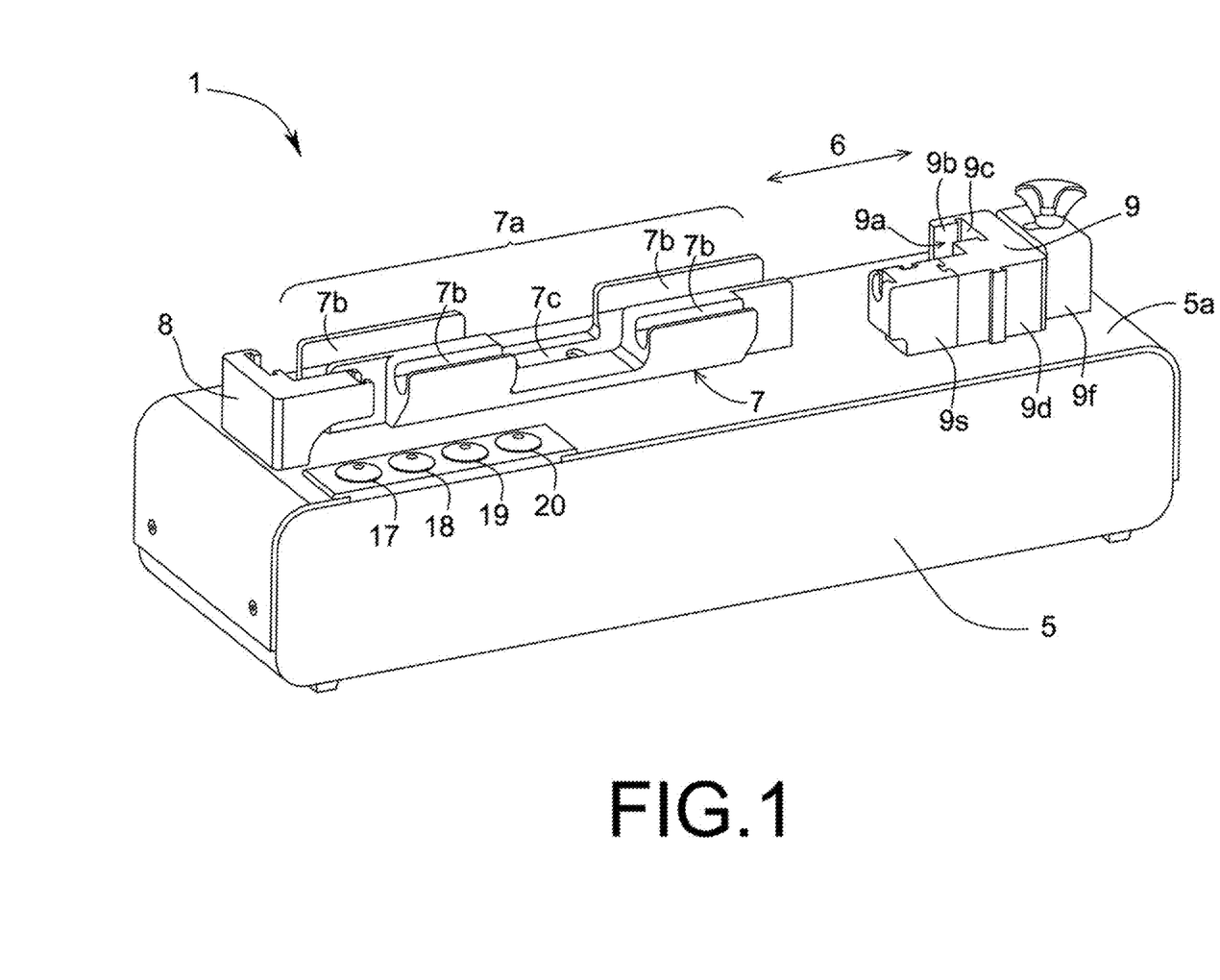
FIG. 1 shows a perspective view of an embodiment of the mixing device according to the invention.
Figure 2:
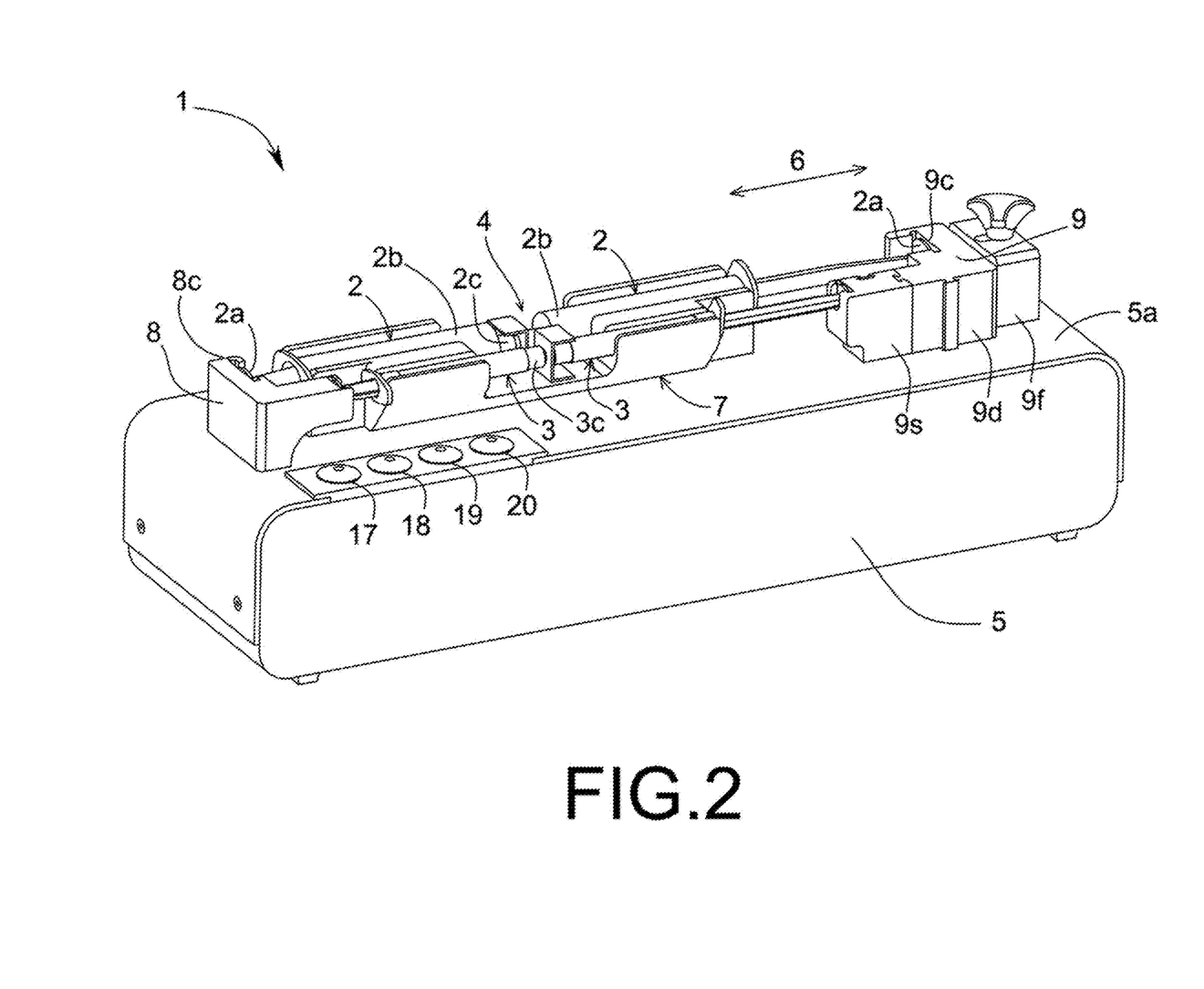
FIG. 2 shows a perspective view of the mixing device of FIG. 1 provided with two pairs of syringes.

A perspective view of an embodiment of the mixing device (1) of the invention is shown in FIG. 1. FIG. 2 illustrates the location of two pairs of faced syringes (2, 3) in the mixing device (1) of FIG. 1. During the normal use of the mixing device (1) normally only one pair of faced syringes is used, i.e. two syringes (2) with a certain volume or two syringes (3) with a smaller volume.

Each syringe (2, 3), an element known in the Prior Art, comprises a tubular body or cylinder (2b, 3b). The cylinder (2b, 3b) is provided with a hole in an injection zone (2c, 3c) located at one end of the respective syringe (2, 3), to allow the entry or exit of the fluid from the cylinder (2b, 3b). This end is usually engaged to a hollow needle or to a connector. By joining them at their ends, it is possible to connect two faced syringes (2, 3), as shown in FIG. 2, for allowing a transfer of fluids between both syringes (2, 3). Each syringe (2, 3) is also provided with a plunger that is longitudinally movable along the inside the cylinder (2b, 3b). The plunger has a support or handle (2a, 3a) at a free end in order to facilitate the displacement, being also provided with a synthetic piston, located inside the cylinder (2b, 3b) and at an end opposite to the handle (2a, 3a). The syringes (2, 3) are usually transparent and can be made of various materials, such as plastic, glass or metal. In the medical field, sterile plastic syringes suitable for medical use are usually used.

Figure 3:
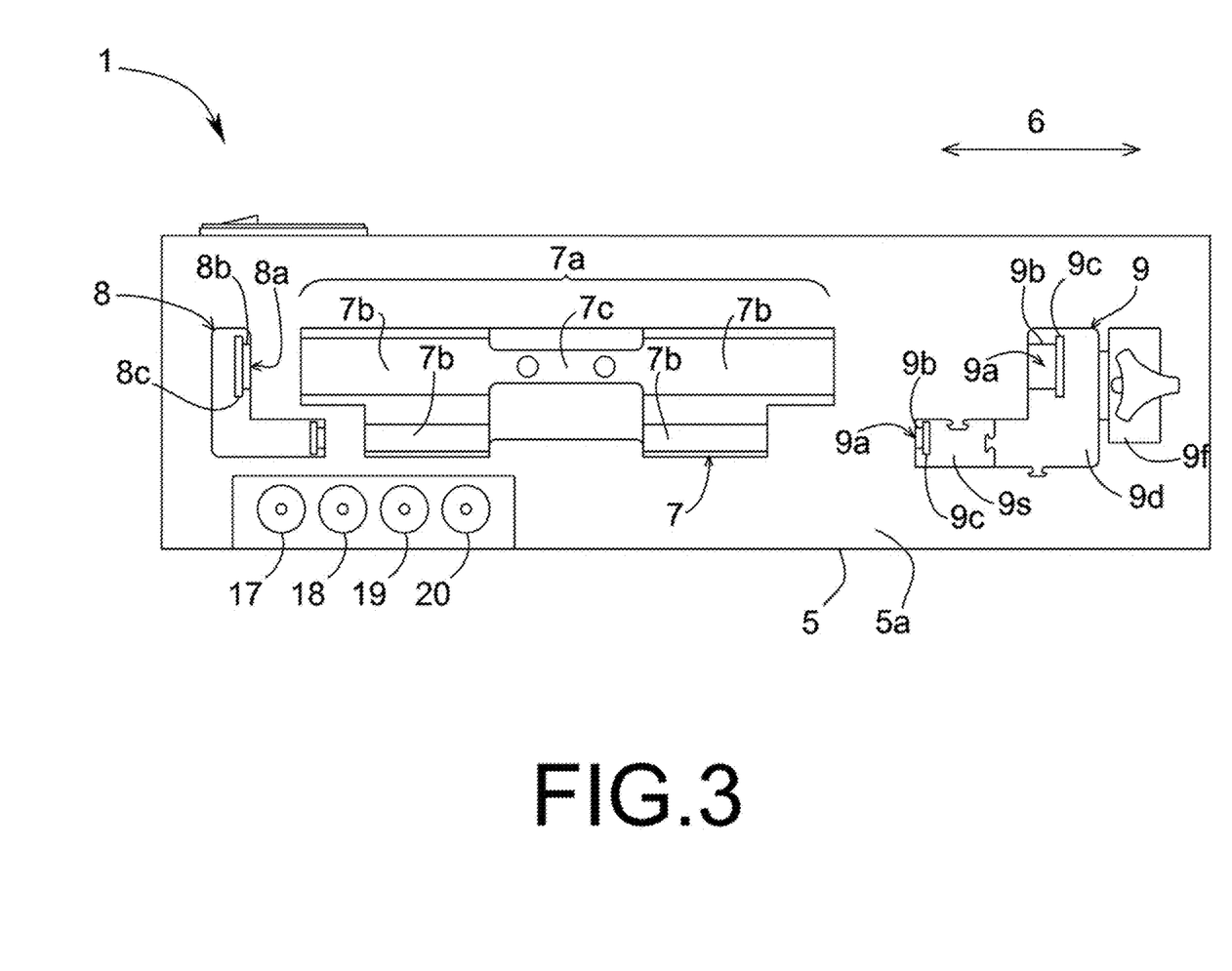
FIG. 3 shows an exploded plan view of the external components of the mixing device of FIG. 1.

FIG. 3 shows a schematic exploded plan view of the external components of the mixing device of FIG. 1.

As shown in the figures, the mixing device (1) comprises at least one mobile carriage (7) movable in a longitudinal direction (6). The mobile carriage (7) has a general dip or cavity (7a) configured to accommodate and hold at least one pair of faced syringes (2, 3), so that they are joined together by a connecting element (4) at their injection zones (2c, 3c) and alignedly arranged in a longitudinal direction (6), as illustrated in FIG. 2.

In the present invention, the definition of transfer must be understood as a complete transfer of the fluid to be mixed between two pairs of faced syringes (2, 3), by means of a complete displacement forwards or backwards of the plungers (2e, 3e) of the syringes (2, 3). A transfer cycle must be understood as the sum of a forward transfer and a backward transfer (i.e., two transfers). The range of a transfer cycle is the distance travelled by the mobile carriage (7) in each transfer, variable depending on the dimensions of the syringes (2, 3).

Additionally, the mixing device (1) comprises at least two fixing elements (8, 9) each one located on a side of the mobile carriage (7). Each of the fixing elements (8, 9) is configured or adapted to accommodate and hold the free end of one of the syringes (2, 3).

In the embodiment in FIGS. 1 and 2, the mixing device (1) has a casing (5) that houses and supports the various components of the mixing device (1). The mobile carriage (7) and the fixing elements (8, 9) are supported on an upper face (5a) of the casing (5) by means of known fixing elements (for example, screws or other alternative fixing means, not shown in the figures). The casing (5) additionally integrates a set of signalling and control elements (17, 18, 19, 20). The casing (5) additionally houses a set of electrical and mechanical components, needed for the correct operation of the device. The configuration of the casing (5) is not especially relevant for the invention, as its parts, manufacturing materials and dimensions may be variable, provided it is suitable for laboratory use and adequately fulfils its function of housing the components of the mixer device (1) and allowing its correct operation.

Figure 4:
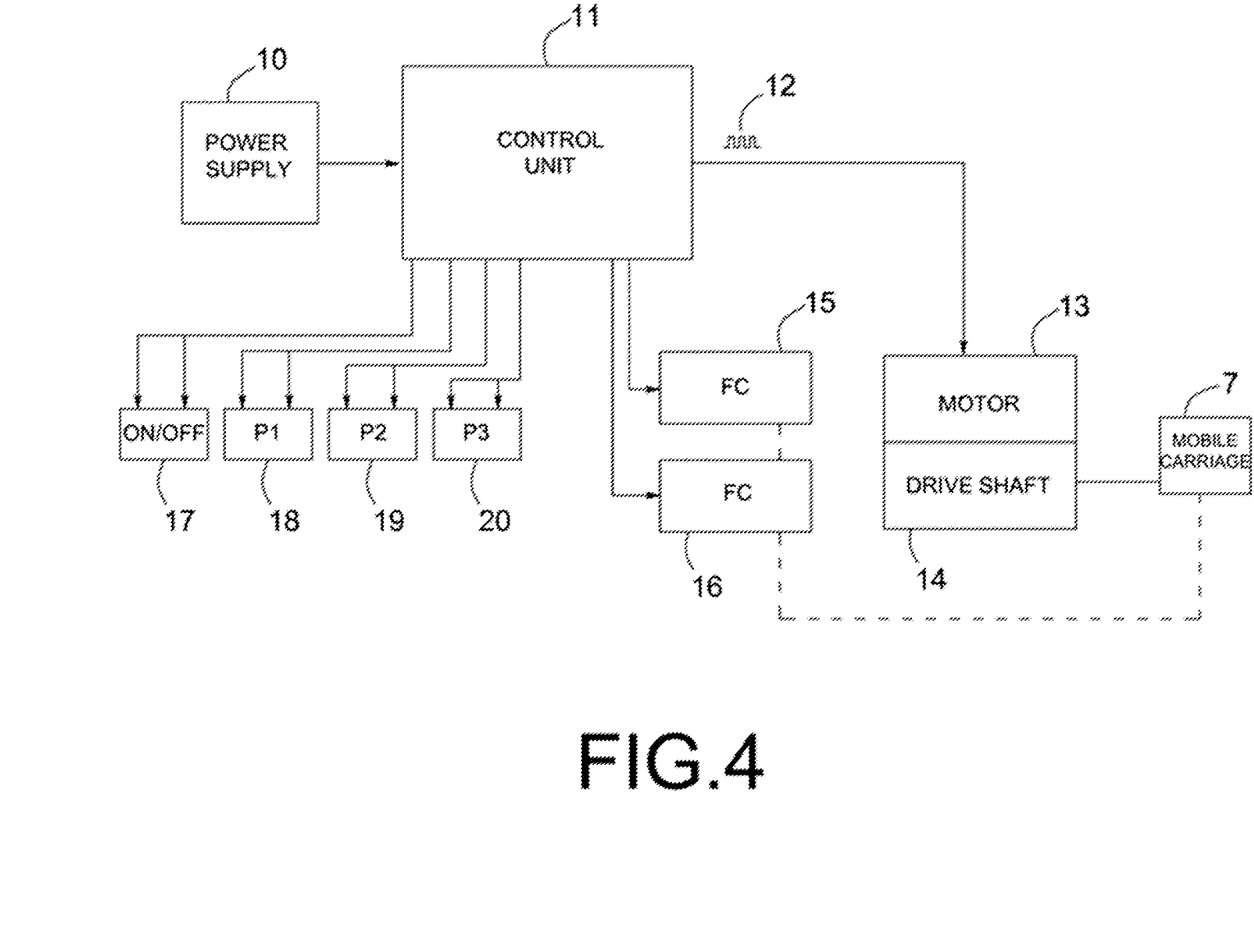
FIG. 4 is a block diagram illustrating the electromechanical operation of the mixing device of FIG. 1.

The mixing device (1) of the invention comprises a control unit (11) communicated with a set of sensors (15, 16) and with a mechanism (13, 14) which transmits a linear displacement to the mobile carriage (7), this transmission being triggered by a control signal generated by the control unit (11). A block diagram of the electronic components of the embodiment of the mixing device (1) corresponding to FIG. 1 is shown in FIG. 4. As illustrated in FIG. 4, the mixing device (1) comprises a 24 DC power supply (10). The control unit (11) comprises a memory with a set of predefined or configurable programmes for controlling the operation of the mixing device (1). The mechanism (13, 14) housed in the casing (5) comprises a motor (13) and a mechanical drive shaft (14). In the particular embodiment of figures, the mixing device (1) optionally uses a stepper motor (13). The control unit (11) generates a pulse signal (12) that controls the rotation of the motor (13). For every 200 pulses the stepper motor (13) rotates one full turn. The rotation of the motor (13) is transmitted to the mechanical shaft (14) engaged to the motor (13). The drive shaft (14), connected to the mobile carriage (7), converts the angular movement of the motor (13) into linear motion. For each turn of the motor (13) the drive shaft (14) makes the mobile carriage (7) move 15 mm.

The set of sensors (15, 16) comprises a calibration sensor (15), for automatic calibration of the range of each transfer. This calibration sensor (15) detects the approach of the mobile carriage (7) and transmits a signal to the control unit (11). The control unit (11) causes a change in the direction of travel of the mobile carriage (7). In this way, the electronics of the mixing device (1) determine the maximum range of a transfer cycle based on the load or percentage of the initial variable filling of the syringe (2). This initial adjustment is called calibration. Optionally, the calibration sensor (15) comprises a limit switch located at one of the fixing elements (8, 9) and a screw located in the mobile carriage (7) for the initial automatic calibration. In alternative embodiments of the invention, other types of mechanical or electronic sensors can be used. The mixing device (1) also includes at least one inversion sensor (16), also communicated with the control unit (11), to reverse the direction of travel of the mobile carriage (7).

In the mixing device (1) of the invention, at least one of the fixing elements (9) has an adjustable configuration. By 'adjustable' it is understood that the fixing element (9) is adapted to accommodate, hold and fix a free end of one of one of the syringes (2, 3) in a initial position that is movable along a longitudinal direction (6). In this way, the distance between the two fixing elements (8, 9) can be adjusted in a variable way. This particular feature of the mixing device (1) is very advantageous since it allows the accommodation of syringes (2) with a variable volume or filling level, whilst keeping an adequate fixing of the handles (2a) of the plungers (2e) of the syringes (2) in both fixing elements (8, 9). It also makes the mixing device (1) compatible with syringes (2, 3) of different lengths and sizes, notably increasing the versatility of the mixing device (1).

In the particular embodiment of the figures, the mixing device (1) specifically comprises a non-adjustable fixing element (8) and an adjustable fixing element (9). Other embodiments are contemplated in which both fixing elements (8, 9) are adjustable.

Figure 5:
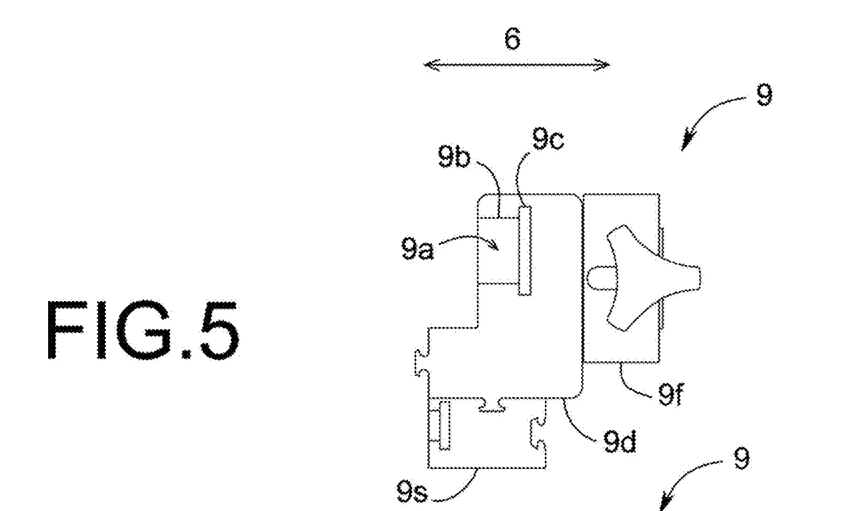
FIGS. 5, 6 and 7 show detailed plan views illustrating the operation of an adjustable fixing element of the mixing device of FIG. 1.
Figure 6:
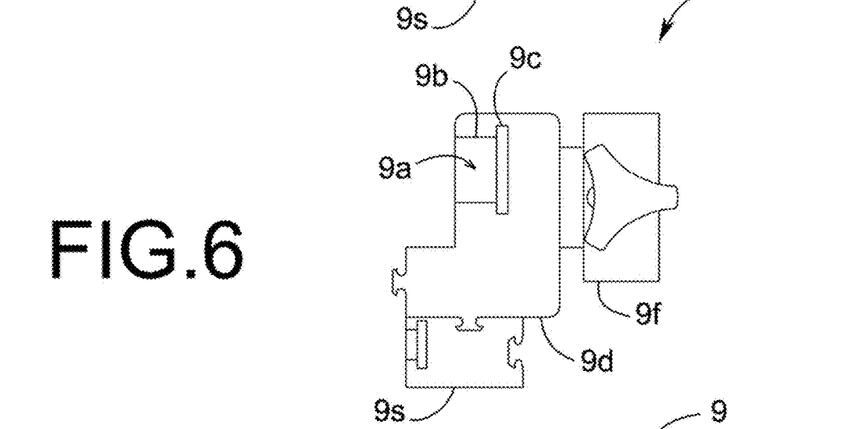
Figure 7:
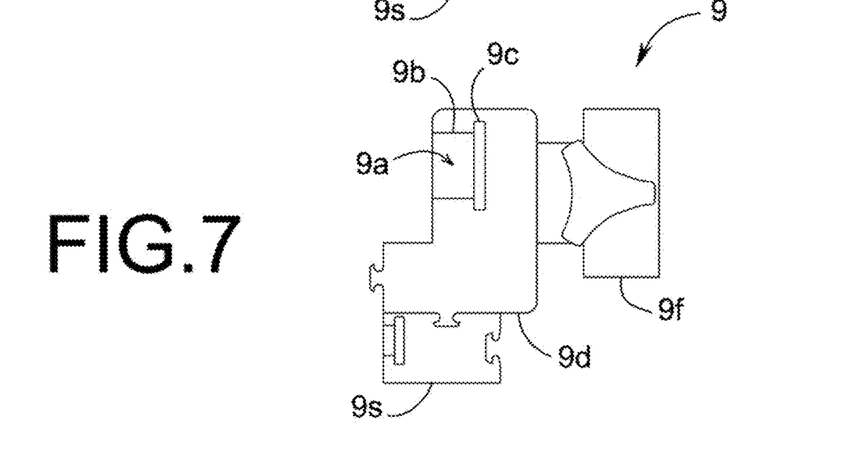
Figure 11:
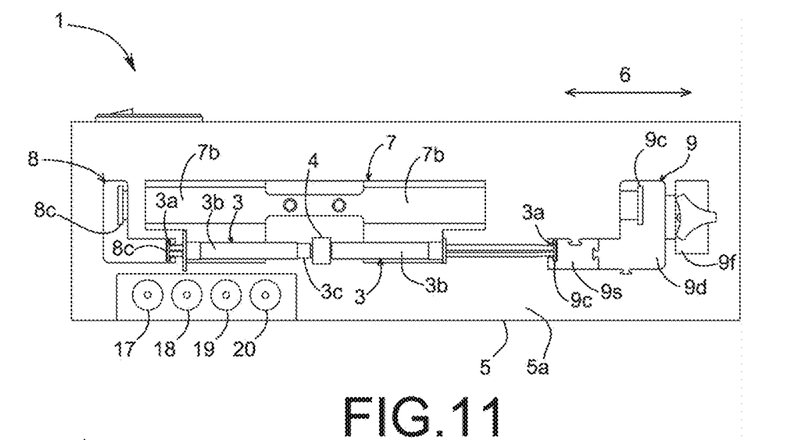
FIGS. 11, 12 and 13 show plan views illustrating the operating sequence of the mixing device of FIG. 1, when part of a transfer between a pair of syringes of a second smaller size is performed.
Figure 12:
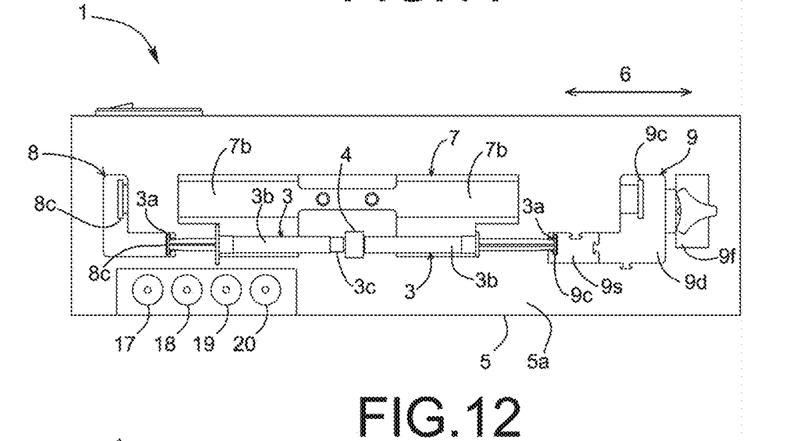
Figure 13:
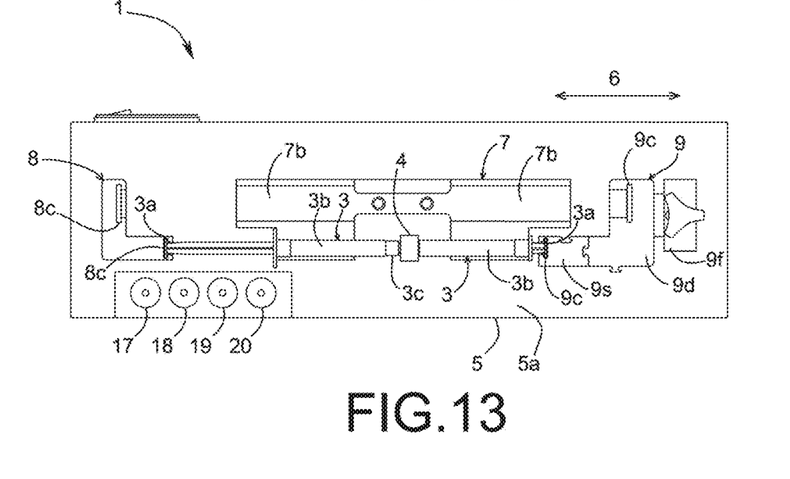

FIGS. 5 to 7 illustrate the operation of an embodiment of an adjustable fixing element (9). Optionally, the adjustable fixing element (9) comprises a fixed part (9o) and a movable part (9d) in the longitudinal direction (6). Also optionally, the fixing elements (8, 9) can have a modular configuration, comprising one or more supplementary parts (8s, 9s) that can be assembled together and/or connectable to the fixing element (9). In the embodiment of the figures, the fixing element (9) comprises both configurations, that is to say the parts (9f, 9d) and the possibility of incorporating supplementary parts (9c), for allowing the adjustment of a variable distance between both fixing elements (8, 9), as illustrated in FIGS. 11 to 13, so that an adequate fitting and fixing of syringes (2, 3) of variable sizes or filling levels is possible.

Additionally, the fixing elements (8, 9) may comprise different mechanisms known in the state of the art, such as rails, slots, fixing screws or other elements. The fixing elements (8, 9) can be made of one or more pieces of any resistant material which is suitable for use in laboratory materials.

Optionally, the casing (5), the mobile carriage (7) and the fixing elements (8, 9) can be made of metal.

Optionally, as in the embodiment of figures, the housing (7a) of the mobile carriage (7) comprises a plurality of cavities (7b) extending along the longitudinal direction (6) and allowing the accommodation, holding and fixing the cylinders (2b, 3b) of the syringes (2, 3) in locations parallel to the longitudinal direction (6). These cavities (7b) are visible in greater detail in FIG. 3. The described embodiment specifically comprises four semi-cylindrical cavities (7b), with a diameter adjusted to the diameter of the syringes (2, 3), to accommodate in this case a first pair of syringes (2) of 20 ml and a second pair of syringes (3) of 3 ml. An intermediate space (7c), adapted for accommodating the connecting element (4) between pairs of the syringes (2, 3), is arranged between each pair of semi-cylindrical cavities (7b).

Optionally, the fixing elements (8, 9) comprise housings (8a, 9a) provided with a semi-cylindrical portion (8b, 9b) and provided with a slot (8c, 9c) adapted to fit and hold the handles (2a, 3a) of the free ends of the syringes (2, 3).

The elements described for the mixing device (1) allow an adequate fit and fixing of the pair of faced syringes (2, 3), so that the mixing of the fluids can be carried out correctly, preventing an undesirable entry of air into the mixture and/or an undesirable formation of foam and bubbles.

Figure 8:
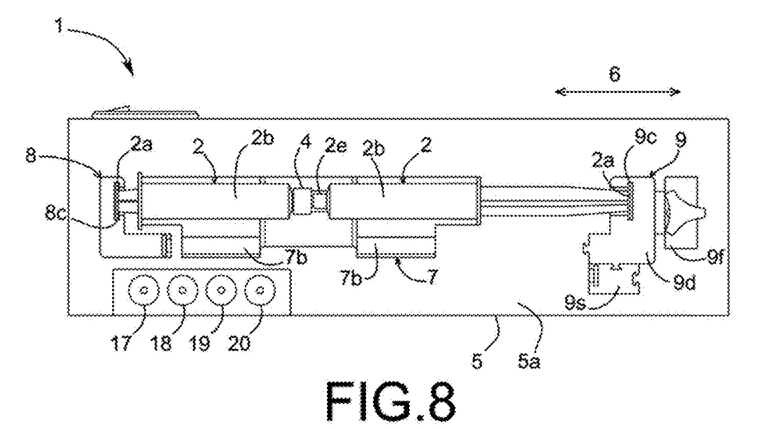
FIGS. 8, 9 and 10 show plan views illustrating the operating sequence of the mixing device of FIG. 1, when half of a transfer between a pair of syringes with a first size is performed.
Figure 9:
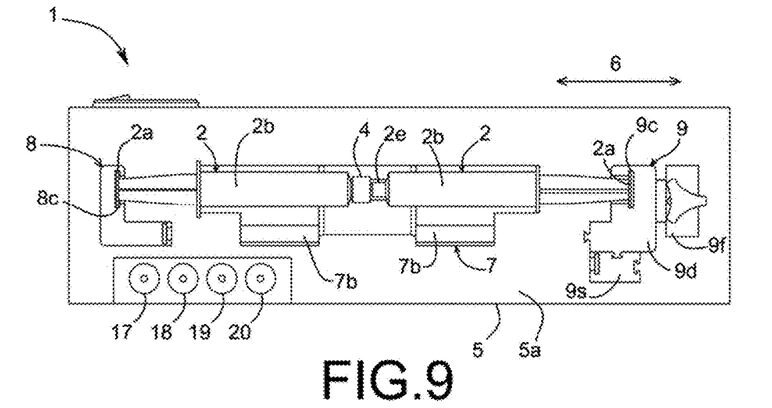
Figure 10:
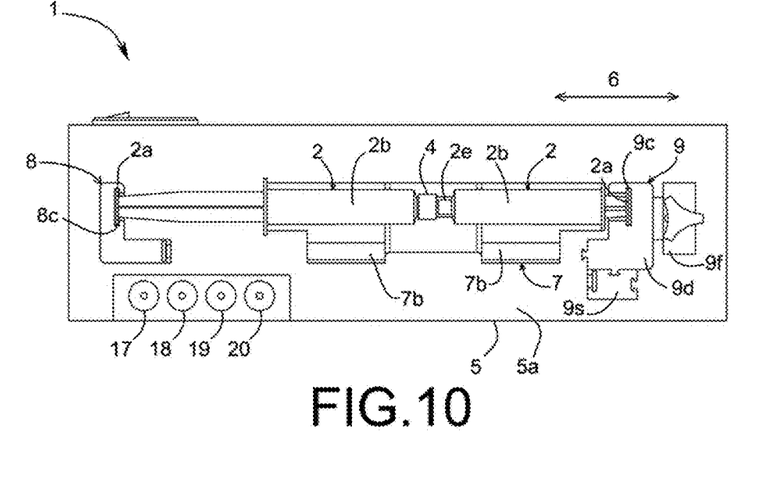

The general operation of the mixing device (1) is described below. Preliminarily, a protocol is carried out to obtain the fluids to be mixed, as will be described in greater detail in several examples included later in this document. FIGS. 8, 9 and 10 show a schematic representation of the sequence of half a transfer between a pair of syringes (2) of 20 ml. Before turning on the mixing device (1), the fluids to be mixed or emulsified are placed in a first syringe (2). A second empty syringe (2) is connected faced with the charged syringe (2), by means of the aligned connection of the pair of syringes (2) faced by their injection zone (2c), using an intermediate connecting element (4). The connecting element (4) between the pair of faced syringes (2) can be of luer-to-luer type, as in the embodiment of the figures, although other types of connecting elements (4) are also possible. Once the two syringes (2) are connected they are placed in the mixing device (1), as illustrated in FIG. 8, fixing their respective cylinders (2*b*) to the mobile carriage (7) and inserting the handles (2*a*) of the plungers (2*e*) into the slots (8*c*, 9*c*) of the fixing elements (8, 9). If necessary, the position of the regulable fixing element (9) will be adjusted according to the length and/or the level of loading or initial filling of the loaded syringe (2). The desired programme is then selected by means of pushbuttons or controls (18, 19, 20) of the casing (5). The start of the selected programme, previously programmed or configured in the internal memory of the control unit (11), is activated by, for example, a start-stop pushbutton (17). Each programme carries out a predefined number of transfers at predetermined speeds. The control unit (11) generates the pulse signal (12) for the stepper motor (13) and the drive shaft (14) transforms the angular movement of the motor (13) into a linear displacement, which is transmitted to the mobile carriage (7). The cylinders (2*b*) of the syringes (2) move simultaneously with the mobile carriage (7), along the longitudinal direction (6). Likewise, the plungers (2*e*) of both syringes (2), fixed to the fixing elements (8, 9), slide internally and longitudinally along the cylinders (2*b*) as the mobile carriage (7) moves. In each transfer (forward and backward movement) the content of a syringe (2) is transferred to the faced syringe (2), so that one syringe (2) becomes emptied while the other is filled. The inversion of the movement to carry out the successive programmed transfers is also controlled by the control unit (11), by a motion inversion sensor (16) installed in a fixing element (8) of the mixing device (1). The procedure described above is similar when using the other pair of syringes (3), smaller in size and calibre, depending on the final product to be obtained. FIGS. 11, 12 and 13 illustrate the positioning and part of the transfer sequence, when syringes (3) of a smaller size and a supplementary piece (9*c*) for the adjustment of the syringes (3) are used.

In the embodiment of the figures and examples, the faced syringes are of the same size and calibre (two 20 ml syringes or two 3 ml syringes). Other embodiments of the mixing device (1) in which the mobile carriage (7) accommodates pairs of faced syringes of different sizes are also contemplated.

Optionally, the mobile carriage (7) and the fixing elements (8, 9) are removable and interchangeable by other mobile carriages and fixing elements, compatible with different sizes of syringes and compatible with each other. This feature makes it possible to configure the mixing device (1) for allowing the assembly of pairs of syringes of different sizes, without the need for all the carriages and fixing elements to be permanently integrated in the mixing device (1). This possibility further increases the versatility of the mixing device (1) even when it is small.

The mixing device (1) admits other variants not shown in the embodiment of the figures. For example, the mixing device (1) may comprise multiple mobile carriages (7) with a parallel arrangement. The mixing device (1) may comprise more than one motor (13) to control the movement of several mobile carriages (7). Other embodiments of the mixing device (1) with a mobile carriage (7) configured to accommodate more than two pairs of faces syringes are also contemplated. Other configurations are possible for the mixing device (1) with multiple mobile carriages (7) each accommodating one or more pairs of syringes of the same size or different sizes.

Also optionally, in other alternative embodiments, a single mobile carriage (7) has a sliding configuration designed to accommodate syringe with variable sizes. For example, the mobile carriage (7) can comprise several slidable coupled parts, according to the length of the pair of syringes. Optionally, the cavities (7*b*) of the mobile carriage (7) can have an adjustable range to accommodate pairs of syringes of variable calibres. In the same way, the intermediate space (7*c*) can have a variable configuration to accommodate connecting elements (4) of different configurations.

Optionally, each mobile carriage (7) can comprise additional auxiliary elements to improve the retention and fixation of the cylinders (2*b*, 3*b*) of the syringes (2, 3) such as caps, handles or other movable elements, which can be opened and closed to prevent the displacement of the cylinders (2*b*, 3*b*) during the operation of the mixing device (1).

In the embodiment of the figures, the casing (5), the mobile carriage (7) and the fixing elements (8, 9) are made of metal. However, the materials and number of parts of the different components of the mixer (1), casing (5), mobile carriage (7) and connecting elements (8, 9) allow variations, as long as they are compatible with the function of the mixing device (1).

The casing (5) may optionally comprise several buttons, selectors, displays or display interfaces and communication systems for monitoring the operation of the mixing device (1). The mixing device (1) can also have an optional lid or cover.

The various detailed optional features show the great versatility of the mixing device (1) of the invention, which admits multiple configurations or variants. These variants are admissible as long as they ensure a correct alignment between the mobile carriage (7) and the fixing elements (8, 9), to allow an adequate accommodation of the syringes (2, 3), so that the mixing of the fluids is correct and tensions that may cause undesirable effects are prevented, such as the breakage of the syringes (2, 3) or their disconnection.

The invention also relates to a method of mixing fluids, by means of successive transfers between syringes with a certain range of transfer, to obtain a final product to be applied to a patient, using the mixing device according to the invention. The mixing method comprises the following steps: loading at least one pair of faced syringes (2, 3) with the fluids to be mixed; placing the pair of syringes (2, 3) in the mixing device (1), fixing their respective cylinders (2*b*) to the mobile carriage (7); adjusting the position of the adjustable fixing element (9) according to the size and/or load of the syringes (2, 3); fixing the handles (2*a*, 3*a*) to the fixing elements (8, 9); and selecting and running a mixing programme, which comprises a predefined number of transfers, with a variable and predetermined speed for each transfer. After the execution of the programme is completed, the pair of syringes (2, 3) are removed.

The invention also relates to the product obtained by this method of mixing and to the use of said product for a medical or dermatological purpose, in particular for the treatment of facial or other types of wrinkles.

EXAMPLES OF THE METHOD ACCORDING TO THE INVENTION

The method of the invention makes it possible to run different programmes which are previously programmed or configurable by the user.

Three non-limiting examples of the method according to the invention will be described below, in order to obtain three different dermatological products. For this purpose, the mixing device (1) of embodiment of FIG. 1 can be used, which, as detailed above, comprises a mobile carriage (7) into which two pairs of syringes of 20 ml (2) or two pairs of syringes of 3 ml (3) can be accommodated respectively. The mixing device (1) of this embodiment has, in particular, three predefined programmes for obtaining three different final products to be applied to a patient: a subdermal gel, an intradermal gel or a serum for topical application. For each of these products, 3 phases will be described: a first phase or protocol for obtaining the fluids to be mixed, a second phase that constitutes the mixing itself and a third phase of product application. The three examples use the mixing device of the invention for the optimal emulsion of two different plasma components, obtained from the blood of a patient: a protein gel and a liquid platelet extract (supernatant). The correct mixing of both components by means of the device and method according to the invention leads to a formulation obtained in a 100% autologous way with in situ preparation.

Figure 14:
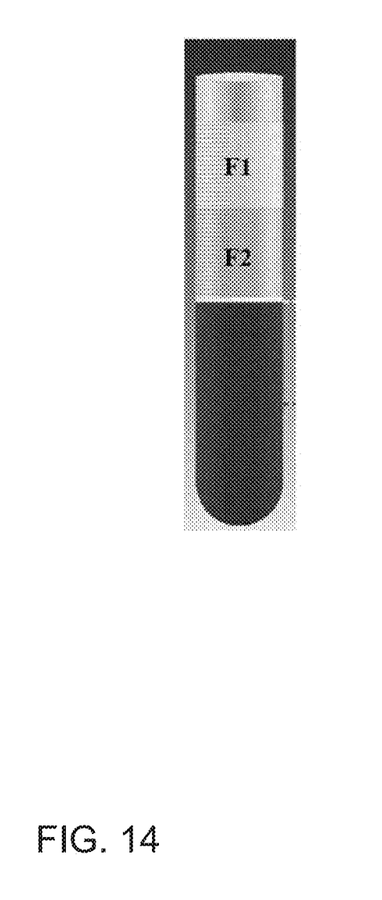
FIG. 14 shows an example of a test tube of blood after centrifugation, from which the fluids to be mixed are obtained.

Example 1: Method for Making a Subdermal Gel According to Programme 1 and Using a Pair of 3 ml Syringes Phase 1: Protocol for Obtaining the Fluids to be Mixed Comprising the following steps:
1. Extraction of blood from the patient. Blood samples are stored in tubes for subsequently obtaining the necessary plasma fractions.
2. Centrifugation, for the separation of blood into the following components (see FIG. 14):
plasma rich in growth factors: the plasma column (F1, F2) contains most of the platelets, distributed according to an increasing concentration gradient, with the number of platelets being lower in the upper part of the tube and greater towards the bottom part of the tube;
white blood cells or leukocytes: this is a thin and whitish layer that is deposited just above the red blood cells;
red blood cells: a column that occupies the lower part of the tube.
3. Fractionation: this includes the extraction of plasma in two tubes (T1, T2) by means of a suction device, for example the BTI® Plasma Transfer Device 2 (PTD®). A protein gel or gel fraction (FG) is obtained, which constitutes the solid phase to be mixed. This gel fraction (FG) is obtained by mixing the fractions (F1, F2) of the first tube (T1) and the fraction (F1) of the second tube (T2). A volume of 2.5 ml of the gel fraction (FG) (F1+F2+F1) is loaded into a 3 ml syringe. Subsequently, a volume of 2 ml of the fraction (F2) is extracted from the tube (T2).
4. Preparation of the protein gel (GP), i.e. the solid phase that will be mixed. This is done by heating the gel fraction (FG) and then resting it at room temperature. The heating and resting times are adapted for the final product to be applied subdermally (around 12 minutes of heating and 5 minutes resting). A BTI® Plasmatherm device can be used for heating.
5. Activation of platelets to obtain the liquid phase to be mixed (supernatant): a volume of 2 ml of the fraction (F2) of plasma extracted from the second tube (T2) is activated with 0.24 ml of PRGF® Endoret® platelet activator and it is then shaken. The platelet-activating agent is intended to release growth factors contained in the platelets. After activation, the formation of a clot in the plasma and its later retraction are allowed, in order to obtain the supernatant. A 3 ml syringe is loaded with 0.5 ml activated plasma (PA), which constitutes the liquid phase to be mixed.

Phase 2: Mixing

Both phases, solid and liquid, obtained in phase 1 are mixed. The 2.5 ml of protein gel (GP) (solid phase) are mixed with the 0.5 ml of activated plasma (PA) or platelet extract (liquid phase or supernatant). For this purpose, phase 2 includes the following steps:
Manually transfer the 0.5 ml of freshly activated plasma (PA) to the syringe with the 2.5 ml of protein gel (GP).
Once the entire volume is available in a 3 ml syringe, connect a second empty 3 ml faced syringe, and accommodate the pair of syringes in the mixing device (1).
Run the programme 1 to obtain a subdermally injectable gel: one pair of 3 ml syringes with a fixed range or displacement of 48 mm per transfer is used; a total of 11 transfers are made at a speed of 300 steps/s or 22.5 mm/s.

Phase 3: Product Application

The pair of syringes is removed and the empty syringe is disconnected. Subsequently an injection needle is placed in the 3 ml syringe containing the mixed product and the subdermal gel is injected into the patient. Subcutaneous infiltration of this product can be used for wrinkle filling and volume increase.

Example 2: Method for Preparing an Intradermal Gel According to Programme 2 and Using a Pair of 3 ml Syringes Phase 1: Protocol for Obtaining the Fluids to be Mixed Steps 1 to 3 are the same as for the previous example 1. In step 4, the times for the preparation of the protein gel (GP) are different for this case of intradermal application (8 minutes heating and at least 5 minutes resting).

Phase 2: Mixing

As in the case of example 1, both solid and liquid phases obtained in phase 1 are mixed. In other words, the 2.5 ml of protein gel (GP) (solid phase) are also mixed with the 0.5 ml of activated plasma (PA) or platelet extract (liquid phase or supernatant). For this purpose, phase 2 comprises the following steps:
Manually transfer the 0.5 ml of freshly activated plasma to the syringe with the 2.5 ml of protein gel.
Once the entire volume is in a 3 ml syringe, connect a second empty 3 ml faced syringe and place the pair of syringes in the mixing device (1).
In this case, run the programme 2 to obtain an intradermally injectable gel: a pair of 3 ml syringes is also used with a fixed displacement of 48 mm per transfer; a total of 90 transfers are made at a speed of 1000 steps/s or 75 mm/s.

Phase 3: Product Application

This steps involves removing the pair of syringes and disconnecting the empty syringe. The product can then be distributed into 3 syringes of 1 ml for intradermal infiltration.

Example 3: Method for Preparing a Serum According to Programme 1 and a Using Pair of 3 ml Syringes

Phase 1: Protocol for Obtaining the Fluids to be Mixed

Comprising the following steps:
1. Extraction of blood from the patient in TP10 BTI® 9 ml collection tubes.
2. Centrifugation, for the separation of blood components. It is recommended to perform the centrifugation with the BTI® System V equipment and at most one hour after the extraction, without refrigerating the blood samples. Blood separation is obtained comprising the three components illustrated in FIG. 14.
3. Fractionation: plasma aspiration contained in the sample collection tubes by means of a PTD2 BTI® aspiration unit. Two TP10 BTI® self-empty tubes are filled by aspirating the entire plasma volume, that is, both fractions (F1, F2) of several centrifuged extraction tubes. Transfer the plasma obtained to a 20 ml syringe.
4. Preparation of the protein gel (gelled plasma): to gel the 20 ml syringe plasma, it must be heated for 12 minutes in a Plasmatherm II device and then left to rest during the following platelet activation step.
5. Activation of platelets to obtain the liquid phase to be mixed (supernatant): 0.02 ml of the PRGF® Endoret® activator will be used for each ml of plasma to be activated. Heat to about 37° C. for about 40-60 minutes in the Plasmatherm II.

Patent ES2633815, in the name of the same applicant as for the present invention, discloses in greater detail a method for obtaining autologous galenic formulations in the form of cream, based on plasma rich in growth factors.

Phase 2: Mixing

Proceed to mix both phases, solid and liquid, obtained in phase 1. For this purpose, the following steps are carried out:
  Transfer the entire volume of supernatant to the 20 ml syringe containing the gelled plasma.
  Once all the fluid to be emulsified is in the 20 ml syringe, connect a second empty 20 ml faced syringe and accommodate the pair of syringes in the mixing device (1).
  Run the programme 3 to obtain a topical application serum: a pair of 20 ml syringes with an adjustable displacement is used. In this programme, since the volume to be mixed is variable and dependent on the patient's blood type, the mobile carriage (7) where the 20 ml syringes used in this protocol are placed is adjustable, although often the range of the transfer can be adjusted to about 74 mm. A limit switch is used to calculate the range in an initial calibration cycle: for this purpose, a transfer cycle (2 transfers, i.e., forwards and backwards) is carried out at a speed of 300 pulses/s, for calculating the range. Subsequently, the mixing is performed. The speeds of this programme 3 (omitting the two recognition transfers mentioned above) are: $1^{st}$ round (2 transfers) at 300 pulses/s, $2^{nd}$ round (2 transfers) at 300 pulses/s, $3^{rd}$ round (2 transfers) at 450 pulses/s, $4^{th}$ round (2 transfers) at 600 pulses/s, $5^{th}$ round (2 transfers) at 750 pulses/s, $6^{th}$ round (2 transfers) at 900 pulses/s, and from the $7^{th}$ round onwards (2 transfers) at 1000 pulses/s. A total of 120 transfers are made.

Phase 3: Product Application

Apply the serum topically. The dispensable serum may be stored in single-dose dispensers or in airless dispensers and preferably at a temperature between 2° C. and 8° C. for prolonged storage periods prior to application.

The invention claimed is:

1. A mixing device, for the mixing or emulsion of fluids, by successive transfers between syringes with a certain range of transfer, the mixing device comprising:
  at least one mobile carriage movable in a longitudinal direction and provided with a housing configured to accommodate and hold at least one pair of faced syringes, the syringes being connected to each other by a first end of each syringe and arranged aligned in the longitudinal direction;
  at least two fixing elements located one on each side of the mobile carriage and adapted to accommodate and retain a second free end of each syringe, wherein at least one fixing element has an adjustable configuration, the fixing element being adapted to accommodate and retain the second free end of the corresponding syringe in a movable position along the longitudinal direction such that a distance between the two fixing elements is variable;
  a set of sensors; and
  a control unit communicated with the set of sensors and a mechanism for the transmission of a linear displacement to the mobile carriage triggered by a control signal generated by the control unit;
  wherein the set of sensors comprises a calibration sensor, for the automatic calibration of the transfer range, and at least one inversion sensor for the inversion of the direction of displacement of the mobile carriage.

2. The mixing device according to claim 1, wherein the adjustable fixing element comprises a fixed part and a movable part (9d) in the longitudinal direction.

3. The mixing device according to claim 1, wherein the adjustable fixing element comprises one or more supplementary parts, wherein the supplementary parts can be assembled together and/or are connectable configured to be connected to the fixing element.

4. The mixing device according to claim 1, wherein the housing comprises a plurality of cavities extending along the longitudinal direction and being adapted to accommodate and hold, in locations parallel to the longitudinal direction, a first pair of equal syringe of a first size and a second pair of equal syringe of a second size, which are smaller than the first pair of syringes.

5. The mixing device according to claim 4, comprising four semi-cylindrical cavities with a diameter adjusted to the diameter of the syringes and an intermediate space, arranged between two semi-cylindrical cavities and adapted for accommodating a connecting element between pairs of syringes by an injection zone located at the first end of the syringes.

6. The mixing device according to claim 5, wherein the connecting element is of a luer-to-luer connector.

7. The mixing device according to claim 4, wherein the fixing elements comprise at least two housings provided with a semi-cylindrical portion and provided with a slot adapted to fit and hold handles of the second free ends of the syringes.

8. The mixing device according to claim 1, wherein the control signal is a pulse signal to control the rotation of a stepper motor and wherein the motor rotation is transmitted to a mechanical drive shaft, engaged to the motor and connected to the mobile carriage, so that the drive shaft converts the angular movement of the motor into a linear displacement in the longitudinal direction, being this wherein the linear displacement is transmitted to the mobile carriage.

9. The mixing device according to claim 1, where the calibration sensor comprises a limit switch arranged in one of the fixing elements and a screw arranged in the mobile carriage.

10. The mixing device, according to claim 1, where the mobile carriage and the fixing elements are removable and interchangeable by other mobile carriages and fixing elements, wherein the other mobile carriages and fixing elements are compatible with different sizes of syringes and compatible with each other.

* * * * *